(12) United States Patent
Mehta et al.

(10) Patent No.: US 11,912,654 B2
(45) Date of Patent: Feb. 27, 2024

(54) PROCESS FOR STEREOSPECIFIC SYNTHESIS OF VITAMIN K2 AND ITS NOVEL INTERMEDIATES

(71) Applicant: SYNERGIA LIFE SCIENCES PVT. LTD., Mumbai (IN)

(72) Inventors: Dilip Mehta, Mumbai (IN); Mayank Shashtri, Lubbock, TX (US); BNS Raju, Hyderabad (IN); Ashwin Shah, Mumbai (IN); Parin Vora, Mumbai (IN); Umakant Mahale, Thane (IN)

(73) Assignee: SYNERGIA LIFE SCIENCES PVT. LTD., Mumbai (IN)

( * ) Notice: Subject to any disclaimer, the term of this patent is extended or adjusted under 35 U.S.C. 154(b) by 0 days.

(21) Appl. No.: 17/733,687

(22) Filed: Apr. 29, 2022

(65) Prior Publication Data

US 2023/0093176 A1    Mar. 23, 2023

(30) Foreign Application Priority Data

Sep. 3, 2021 (IN) .............................. 202121040002

(51) Int. Cl.
*C07C 46/06* (2006.01)
*C07C 317/14* (2006.01)

(52) U.S. Cl.
CPC ............ *C07C 46/06* (2013.01); *C07C 317/14* (2013.01)

(58) Field of Classification Search
USPC ........................................................ 568/33
See application file for complete search history.

(56) References Cited

U.S. PATENT DOCUMENTS

| | | | |
|---|---|---|---|
| 4,089,873 | A | 5/1978 | Rapoport et al. |
| 4,199,531 | A | 4/1980 | Terao et al. |
| 4,229,356 | A | 10/1980 | Tabushi et al. |
| 4,603,223 | A | 7/1986 | Ruttimann et al. |
| 7,718,407 | B2 | 5/2010 | Benedetti et al. |
| 8,114,642 | B2 | 2/2012 | Takaoka et al. |
| 9,512,153 | B2 | 12/2016 | Moller et al. |
| 10,159,687 | B2 | 12/2018 | Moller et al. |

FOREIGN PATENT DOCUMENTS

| | | |
|---|---|---|
| CN | 10113927 A | 3/2008 |
| CN | 102351677 A | 2/2012 |
| EP | 2346806 B1 | 7/2011 |
| JP | H065370 B2 | 3/1992 |
| WO | WO 2010/035000 A1 | 4/2010 |
| WO | WO 2011/117324 A2 | 9/2011 |

OTHER PUBLICATIONS

Masaki, Yukio; Chemical & Pharmaceutical Bulletin (1984), 32(10), 3959-67.*
Coates et al, Stereoselective Isoprenoid Chain Extension With Acetoacetate Dianion: (E, E, E)-Geranylgeraniol From (E, E)-Farnesol, Organic Syntheses, vol. 84, p. 43-57 (2007).
Isler et al., Synthese und Isolierung von Vitamin Kz und isoprenologen Verbindungen, Helv. ChimActa 1958, 41, 786-807 (German Only).
Isler et. al. Uber Die Vitamine K1and K2, Angew. Chem., 71. (Jan. 1959) No. 1, pp. 7-15 (German Only).
Knauer TE, et al., Metabolism and biological activity of cis- and trans-phylloquinone in the rat, J Nutr. Dec. 1975; 105(12):1519-24. doi: 10.1093/jn/105.12.1519. PMID: 1195014.
Min JH, et al., The Friedel-Crafts allylation of a prenyl group stabilized by a sulfone moiety: expeditious syntheses of ubiquinones and menaquinones, J Org Chem. Oct. 3, 2003;68(20):7925-7. doi: 10.1021/jo0350155. PMID: 14510583.
Naruta, Y, Regio- and Stereoselective Synthesis of Coenzymes Qn (n = 2-10), Vitamin K, and Related Polyprenylquinones, J. Org Chem, Mar. 1980, 45, 4097-4104.
Suhara Y, et al., Efficient synthesis and biological evaluation of omega-oxygenated analogues of vitamin K2: study of modification and structure-activity relationship of vitamin K2 metabolites. Bioorg Med Chem Lett. Mar. 15, 2007;17(6):1622-5. doi: 10.1016/j.bmcl. 2006.12.082. Epub Jan. 4, 2007. PMID: 17239598.
Singh, et al., Micellar Catalysis TT45 + TT2S Cycloaddition in Aqueous Media, Organic Chemistry Syn. Com, (1988), 18 (6), 567-574.

\* cited by examiner

*Primary Examiner* — Ana Z Muresan
(74) *Attorney, Agent, or Firm* — Bryan D. Zerhusen; Nicholas R. Herrel; CANTOR COLBURN LLP

(57) ABSTRACT

The present disclosure relates to a novel process for the synthesis of stereospecific compounds of Vitamin K2 group in general and Vitamin K2-7. The present disclosure further discloses novel intermediates useful in the synthesis of stereospecific Vitamin K2-7. Compounds of the Vitamin K2 group obtained are crystalline and exhibit well defined melting points.

3 Claims, No Drawings

PROCESS FOR STEREOSPECIFIC SYNTHESIS OF VITAMIN K2 AND ITS NOVEL INTERMEDIATES

CROSS-REFERENCE TO RELATED APPLICATIONS

This application claims priority to and the benefit of Indian Patent Application No. 202121040002, filed 3 Sep. 2021, titled A PROCESS FOR THE STEREOSPECIFIC SYNTHESIS OF VITAMIN K2 AND ITS NOVEL INTERMEDIATES, which is incorporated herein in by reference in its entirety for all purposes.

FIELD OF INVENTION

This disclosure relates to a novel process for the synthesis of stereospecific compounds of Vitamin K2 group in general and Vitamin K2-7, in particular. The disclosure also discloses novel intermediates useful in the synthesis of stereospecific Vitamin K2-7.

BACKGROUND OF THE INVENTION

Compounds of Vitamin K group are not produced by human tissue. They are commonly found in green plants, e.g., green leafy vegetables such as spinach, broccoli, cabbage, lettuce, and green tea. Compounds of Vitamin K2 group are synthesized by bacteria and are present in fermented food products, like cheese, yogurt, sauerkraut and meat. Vitamin K2-7 is found in fermented soybean seeds. Since vitamin K2-7 is produced by intestinal bacteria, the human body has enough of vitamin K2-7. However, a long-term treatment with sulphonamides and antibiotics may cause deficiency of the beneficial intestinal microflora (avitaminosis or hypovitaminosis). Vitamin K2-7 deficiency can lead to bleeding, coagulation dysfunctions, and osteoporosis.

Vitamin K group of compounds which share a common methylated naphthoquinone ring structure, vary in the number of isoprene units at the 3-position and are named according to the number of prenyl units therein. Thus, Vitamin K2-7 has seven prenyl residues in trans form. Naphthoquinone is the main functional group of the vitamin K2 group of compounds and the mechanism of action is similar. However, intestinal absorption, transport, tissue distribution, and bio-availability depend on the length of the prenyl chain. Vitamin K2-7 is fat soluble and has a circulation half-life of three days. While Vitamin K2-7 occurs naturally in various vegetables and is produced by the bacteria in the intestines, there is a need to develop synthetic routes for Vitamin K2-7 for the patients suffering from Vitamin K2-7 deficiency. Researchers have attempted both biotechnological and synthetic chemistry routes for the synthesis of Vitamin K2-7.

Several approaches have been proposed in the past to isolate/synthesize compounds of the Vitamin K2 group, especially Vitamin K2-7. In the early days, Vitamin K1 and K2 were extracted from natural resources. JP 2443031 B2 described a method for producing Vitamin K concentrate from a deodorized distillate of the vegetable oil. Administration of Vitamin K2 producing bacteria such as the bacteria of the intestinal flora more particularly by the bacteria of the species *Escherichia coli*, *Bacillus subtilis* and *Bacteroides* subsp. WO 2008/040793 described that *Bifidobacterium*, *Lactococcus*, Leucon Stoc, *Enterococcus* and *Propionibacterium* were more efficient in the production of compounds of Vitamin K2 group than their corresponding wild type strains.

EP2419506 B1 described bacterial strains of *Lactococcus facus* subsp. creminis CNCMI-4128, DSM 23476, DSM 23477, DSM 23478, and DSM 23479 which produced at least 12 µg of Vitamin K2 compounds per 100 g of milk.

U.S. Pat. No. 7,718,407 B2 described a process for the preparation of vitamin K2-7 using the culture of *Bacillus subtilis* mutant strain GN13/72DSM17766.

U.S. Pat. No. 8,114,642 B2 disclosed a method for producing vitamin K2 group of compounds by culturing *Bacillus natto* in a liquid medium to obtain a *Bacillus natto* culture.

In the case of Vitamin K2 group of compounds, a "lack of biological activity" was ascertained for the cis form, in the journal, J. Nutrition 105: 1519-1524, 1975. According to O. Isler et. al. in Angew. Chem., 71. (1959) no. 1 pages 13-15, in the case of substances of the Vitamin K1 and K2 group, the mono cis compounds (cis double bond adjacent to the naphthoquinone ring system) showed, a significantly lower activity than the all trans form.

Chemical synthesis allows the preparation of a particular compound of Vitamin K2 group rather than the isolation of a mixture of different Vitamin K2 s. Subsequent methods were focused on obtaining a specific Vitamin K2, especially Vitamin K2-7, in all trans form. First chemical synthesis of Vitamin K2-7 was reported by Isler et al. Hely ChimActa 1958, 41, 786-807. Suhara et al, Bioorg Med Chem Lett 17, (2007) 1622-1625, described syntheses of Vitamin K2 analogues wherein the terminal methyl group was converted to a hydroxyl, aldehyde or acid group. Naruta, J Org Chem 1980, 45, 4097-4104, described the synthesis of Vitamin K2 analogues using trialkylallylstannane to link the preformed side-chain to the naphthoquinone group.

Min et al. (J. Org. Chem. 2003, 68, 7925-7927) described the Friedel-Crafts allylation of a prenyl group stabilized by a sulfone moiety. The reference further related to the synthesis of ubiquinones and menaquinones from the resulting protected p-hydroquinone containing the C5 trans-allylic sulfone moiety.

U.S. Pat. No. 4,089,873 described the preparation of Vitamin K2 group of compounds using a copper-mediated coupling reaction. U.S. Pat. No. 4,199,531 described the preparation of quinones using arylsulfonyl/halogen coupling chemistry. The side chain of menadiol derivative having at position C-3 from 1 to n terminal activated isoprenyl units, accomplished by its stereo- and regio-selective alkylation with activated side chain precursor consisting of m isoprenyl units. The carbanion generated under basic conditions on the carbon atom adjacent to aryl thio, aryl sulfinyl or aryl sulfonyl terminal group of one substrate was subsequently alkylated with alkyl halide as the second substrate. In the case of the reaction of monoprenyl menadiol aryl sulfonyl derivative with polyprenyl halide, the product was subjected to reductive desulphonation, deprotection of the hydroxyl groups if there was a need thereof, and/or oxidation to afford Vitamin K2 derivative.

According to the inventors of U.S. Pat. No. 4,603,223, the then known processes for the manufacture of Vitamin K2 related compounds which started from hydroquinones or monoacylated hydroquinones were unsatisfactory, since a relatively large number of reaction steps were involved. Processes starting from, menadione itself or a readily accessible derivative thereof were then unknown. The patent described synthesis of substituted 2 methylquinone/2 methyl naphthoquinone, cyclopentadiene adduct which was then prenylated in 3 position and the prenylated derivative of the menadione cyclopentadiene adduct was subjected to a Retro Diels Alder reaction, to isolate the desired vitamin K compound, wherein the stereo specificity of the prenyl side chain was maintained.

The process comprises reacting a compound of (1)

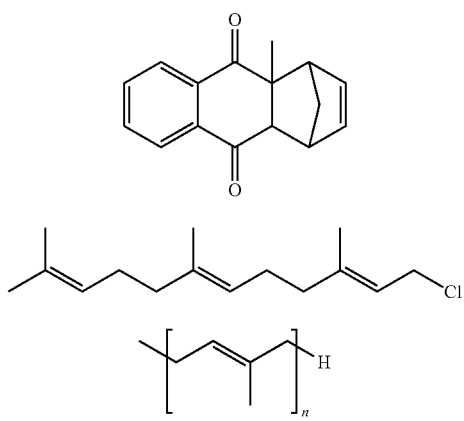

with a compound of (2) farnesyl chloride or a group of the compounds (3) wherein n is an integer from 0 to 10, and converting the compound of (4) into a compound of the Formula I (provided below as 5).

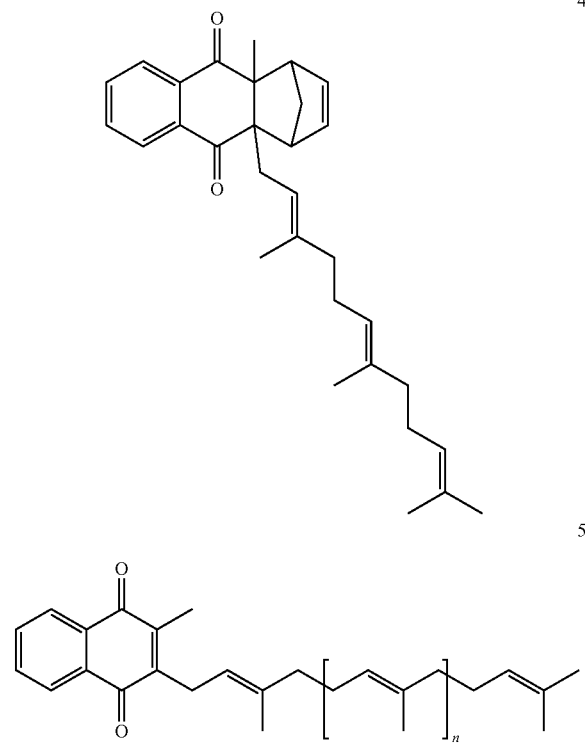

Formula I (shown as 5) thus represents compounds of the vitamin K group, such as K2-5, K2-10 wherein the n is 3 and 8 respectively depending on the value of n. The reaction of a compound of (1) with a compound of (2) was carried out in an inert organic solvent and in the presence of a strong base. Both polar and apolar aprotic solvents could be used. Aliphatic or aromatic hydrocarbons such as hexane, benzene, toluene, were preferred. The preferred polar protic solvent was t-butanol.

The reaction could be carried out at a temperature of about −20° C. to about −30° C., preferably at about −5° C. to about −10° C. and especially at about 0° C. to −5° C.

Chinese patent CN 102351677A described the catalytic hydrogenation of 2 methyl 1,4 naphthoquinone to 2 methyl 1,4 hydro naphthoquinone followed by Friedel Craft's alkylation with geraniol and the oxidation of the alkylated product to yield Vitamin K2-2.

U.S. Pat. No. 4,229,356 disclosed the reaction of 2 methyl 1,4 hydro naphthoquinone compound with a compound selected from phytyl halide, isophytyl halide, geranyl halide, farnesyl halide, geranyl geranyl halide, preferably bromide in a heterogeneous medium comprising a quaternary ammonium ion or a tetra alkyl phosphonium ion followed by the oxidation of the resulting hydro precursor to yield the corresponding Vitamin K2.

Chinese patent CN 10113927A disclosed condensation of Vitamin K3 with the halide obtained from an alcohol in the presence of a catalyst to yield the corresponding Vitamin K2. The Japanese patent JPH0653 70B2 disclosed a method for separating Vitamin K2 isomers using supercritical solvents and ionic liquids.

Preparing Vitamin K2 group of compounds having different numbers of isoprenoid units and maintaining the stereo specificity of the sidechain is a challenging task. Methods have been developed to maintain selectivity by extending one isoprenoid unit at a time. (Coates et al Org. Synth. 2007, 84, 43-57). However, the yield and stereo specificity decreased each time a prenyl unit was added.

During the synthesis of Vitamin K2-7, the Kumada coupling is used twice. Synthesis of Vitamin K2s, containing more than 7 isoprenoid units or more, required at least one reactant containing 4 or more isoprenoid units which were not readily available and needed to be synthesized.

Vitamin K2-7 could be synthesized by either of the following methods. 1) attachment of heptaprenyl chain directly to menadiol molecule, i.e, "0+7" strategy; 2) attachment of shorter chain fragments to monoprenyl derivative of menadiol, "1+n+m" strategy; and 3) attachment of hexaprenyl chain to monoprenyl derivative of menadiol, i.e, "1+6" strategy.

EP 2917171 B1 described the synthesis of Vitamin K2-7 using 1+6 strategy. The patent described the synthesis of Synthon A as the ethoxy protected monoprenyl menadiol, having the terminal phenylsulfonyl function in allyl moiety attached in position C-3. Synthon B was hexaprenyl halide containing a phenylsulfonyl group —SO2Ph. Coupling of synthons A and B in the alkylation reaction resulted in a vitamin K2-7 derivative, possessing a phenylsulfonyl group in heptaprenyl chain and hydroxyl groups protected in the ether form. Vitamin K2-7 was obtained on the removal of phenylsulfonyl groups, deetherification and oxidation.

WO 2011117324A2 reported a new procedure for the synthesis of polyphenols, which when reacted with appropriate menadione derivatives through Kumada synthesis or Suzuki coupling led to compounds of Vitamin K2 group. Pentaprenyl alcohol was synthesized from diprenyl-alcohol bromide, having protected acetyl and phenylsulfonyl triprenyl groups, After, each step of the process: alkylation, desulfonylation and removal of hydroxyl protecting groups, purification of the product by silica gel flash chromatography was necessary. Polyprenyl halides obtained according to this procedure were used in the synthesis of Vitamin K2-7, under Grignard/Kumada or Suzuki conditions, following "0+7" or "2+5" strategy.

WO 2010/035000 A1 disclosed the synthesis of vitamin K2-7 based on the polyprenyl ring attachment to the protected activated menadiol derivative, under Grignard/Kumada or Suzuki conditions, according to "0+7 strategy".

EP 2346 806 B1 described the synthesis of novel intermediate compounds and of a compound that formed part of vitamin K2 group. The patent described the synthesis of a precursor for -E polyprenyl side chains using Biellmann chemistry. This involved the formation of phenythio or phenylsulfonyl substituted compounds and reaction of these sulphur compounds with an electrophile, such as a halide, in the presence of a base. The polyprenyl unit was reacted with a protected menaquinone derivative prepared using either Kumada or Suzuki coupling reaction. The phenythio or phenylsulfonyl derivatives were reduced using lithium metal or a metal hydride. The molecule was then deprotected and oxidized using ceric ammonium nitrate to obtain the desired Vitamin K2 compound. The strategy used herein for the synthesis of Vitamin K2-7, was 2+5 strategy, which the patentees claimed yielded better stereochemistry and resulted in solid, crystalline Vitamin K2-7. By using a double Bielmann coupling or triple Bielmann coupling, Vitamin K2 s of increasing chain length could be prepared. Another benefit according to the patentees was that the selenium dioxide reduction step used to form the naphthoquinone reactant took place more readily on a naphthoquinone carrying on 2 isoprenoid units than on a longer chain molecule.

In view of the stability issues associated with Vitamin K2-7, efforts have been made to synthesize prodrugs of Vitamin K2-7, which produce Vitamin K2-7 in the body. U.S. Pat. Nos. 9,512,153 B2 and 10,159,687 B2 described the conversion of diketone of Vitamin K2 in to a monosubstituted or disubstituted ester which was converted to Vitamin K2-7 in the body.

DETAILED DESCRIPTION

A scrutiny of the prior art reveals that more emphasis is being laid on the new chemical routes to the synthesis of Vitamin K2 group, especially Vitamin K2-7, which would be in all trans form, involve minimal number of steps, use readily available raw materials, avoid extreme reaction conditions, maximize yield and minimize impurities. The inventors of the present disclosure have surprisingly found that the reaction of menadione cyclopentadiene adduct with a prenyl chloride in the presence of a solvent mixture containing 10-20% t-butanol in toluene by volume, minimizes the formation of impurities in the reaction product.

According to an embodiment of the disclosure a menadione cyclopentadiene adduct is formed in the presence of a phase transfer catalyst (Cetyl Trimethyl Ammonium Bromide), which shortens the reaction time and enhances the yield of the adduct.

According to another embodiment of the disclosure the menadione/cyclopentadiene adduct is reacted with farnesyl chloride in a toluene/t-butanol mixture wherein the solvent composition has a significant influence on the yield of the Vitamin K 2-3/cyclopentadiene adduct formed. This composition is completely different from that described in the prior art resulting in higher yield.

According to another embodiment of the disclosure the Vitamin K 2-3 is recovered from the vitamin K2-3 cyclopentadiene adduct by subjecting the latter to retro Diels alder reaction.

According to another embodiment of the disclosure Vitamin K 2-3 is further reacted with alkyl halides selected from methyl, ethyl, benzyl halides in the presence of the phase transfer catalyst to protect the keto group and complete the reaction in a shorter time. The methodology is further illustrated using benzyl chloride. This strategy is particularly useful when the prenyl halide corresponding to the side chain in the Vitamin K2 group is not commercially available as in the case of Vitamin K2-7.

In yet another embodiment of the disclosure the benzyl protected Vitamin K 2-3 is further reacted with N bromo succinimide to obtain the bromohydrin of the protected Vitamin K 2-3.

In yet another embodiment of the disclosure the benzyl protected Vitamin K 2-3 bromohydrin is further reacted with Potassium carbonate to obtain the Epoxide of the protected Vitamin K 2-3.

In yet another embodiment of the disclosure the benzyl protected Vitamin K 2-3 epoxide is further converted in to corresponding alcohol in the presence of aluminium isopropoxide.

In yet another embodiment of the disclosure, the benzyl protected Vitamin K 2-3 alcohol is converted into the corresponding chloride by treatment with thionyl chloride.

In yet another embodiment of the disclosure, the benzyl protected Vitamin K 2-3 chloride is treated with Geranyl geranyl phenyl sulphonate under PTC (Phase Transfer Catalysis) to obtain benzyl protected Vitamin K 2-7 bearing a SO2Ph group on the $16^{th}$ carbon atom. PTC has several advantages, including:

a. expensive anhydrous or aprotic solvents are avoided,
b. reaction promotes higher yield while suppressing side reactions,
c. the reaction is carried out at room temperature, and
d. the reaction avoids the use of various alkoxides, sodamide, sodium hydride, or metallic sodium.

In yet another embodiment of the disclosure, the benzyl protected Vitamin K 2-7 bearing a SO2Ph group on the $16^{th}$ carbon atom is treated with (1, 3 Bis (diphenyl phosphino) propane) palladium chloride II chloride and Super hydride to effect desulphonation of the $16^{th}$ carbon atom followed by debenzylation of the protected keto group with Ceric Ammonium Nitrate (CAN) to obtain Vitamin K 2-7.

In yet another embodiment of the disclosure, the benzyl protected Vitamin K 2-4 chloride is treated with Farnesyl phenyl sulphonate under PTC (Phase Transfer Catalysis) to obtain benzyl protected Vitamin K 2-7 bearing a SO2Ph group on the $21^{st}$ carbon atom.

In yet another embodiment of the disclosure, the protected Vitamin K 2-7 bearing a SO2Ph group on the 21st carbon atom is treated with (1, 3 Bis (diphenyl phosphino) propane) palladium II chloride and Super hydride to effect desulphonation of the $21^{st}$ carbon atom followed by debenzylation of the protected keto group with Ceric Ammonium Nitrate (CAN) to obtain Vitamin K 2-7.

In yet another embodiment of the disclosure the dibenzyl ether of Vitamin K 2-3 chloride and dibenzyl ether of Vitamin K 2-4 chloride are treated with prenyl sulphonates bearing varying prenyl units and SO2Ph groups at various carbon positions, subjected to desulphonation and debenzylation to obtain Vitamin K 2-6, K 2-7, K2-8, and higher members of the series.

The various steps involved in the synthesis of Vitamin K2, more particularly, vitamin K2-7 are described below.

Step 1: Preparation of Menadione Adduct

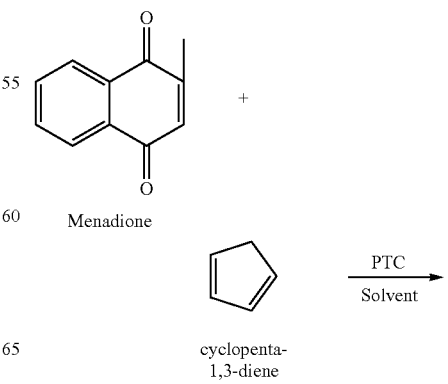

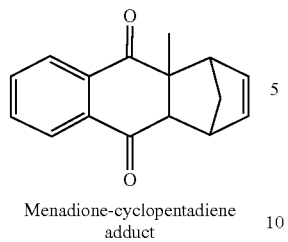

Menadione-cyclopentadiene adduct

Cyclopentadiene adduct of menadione was prepared, according to the research publication of one of the inventors (V. K. Singh, et al Syn. Corn, (1988), 18 (6), 567-574, under micelle catalyzed Diels-Alder reaction conditions, which enhanced reaction yields and shortened reaction times.

Step 2: Preparation of Farnesyl Chloride

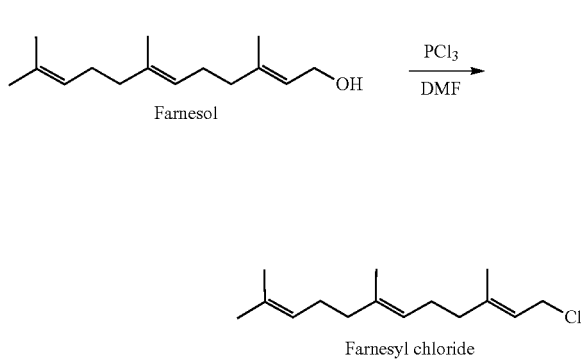

Farnesol was dissolved in DMF and chlorinated using phosphorous trichloride at ambient temperature.

Step 3: Preparation of Vitamin K2-3 Cyclopentadiene Adduct

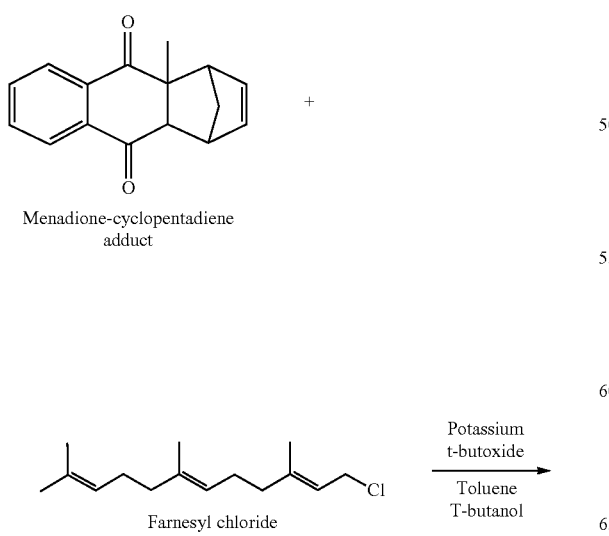

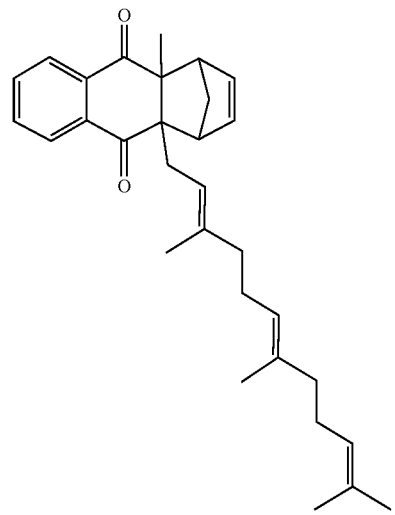

K2-3 Adduct

The reaction was carried out in the presence of Potassium t-butoxide in toluene and tert-butanol mixture solvent using Farnesyl Chloride. It was surprisingly discovered that there existed a t-butanol-toluene composition range (10:90 to 20:80 v/v), not disclosed in the prior art, which resulted in the presence of the minimum amount of impurity in the mixture Step 4: Preparation of Vitamin K2-3

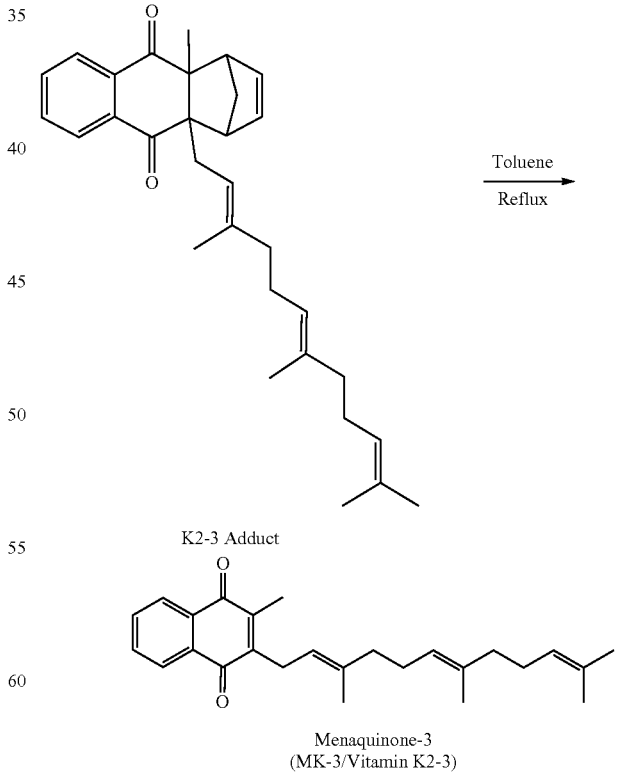

Vitamin K2-3 was recovered from the Vitamin K2-3 cyclopentadiene adduct by refluxing adduct in toluene.

Step 5: Preparation of Dibenzyl Ether Vitamin K2-3

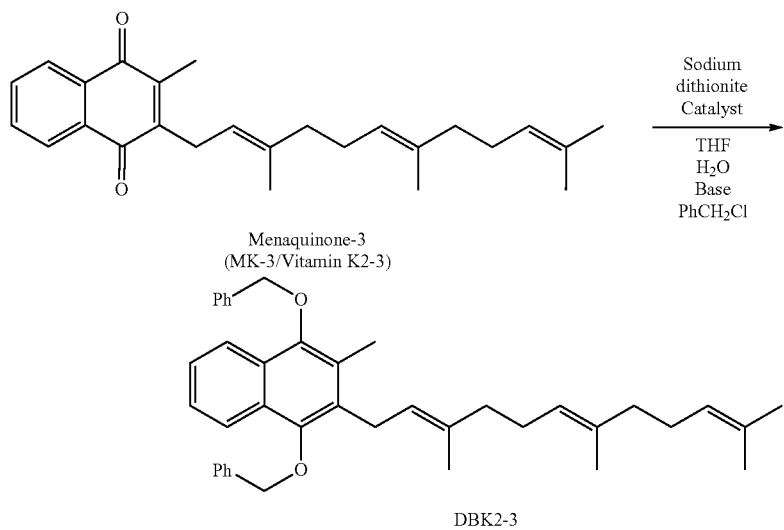

The reaction was carried out under (PTC) phase transfer catalysis. The product was dissolved in THF. Sodium dithionite dissolved in water was added to the reaction mass under inert atmosphere. After completion of reaction unreacted reagent was neutralized with sodium bicarbonate. It was further treated with aqueous potassium hydroxide solution and benzyl chloride. After completion of the reaction, THF was distilled off followed by extraction with a suitable solvent to yield Dibenzyl ether Vitamin K2-3.

Step 6: Preparation of Dibenzyl Ether Vitamin K2-3 Bromohydrin

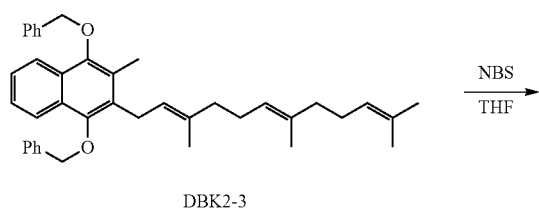

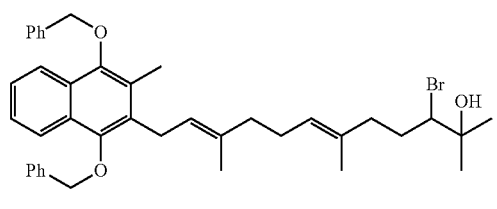

The reaction was carried out using THF as solvent in presence of NBS (N-Bromo Succinimide). After completion, excess bromine was destroyed using sodium thiosulphate followed by extraction with ethyl acetate.

Step 7: Preparation of Dibenzyl Ether Vitamin K2-3 Epoxide

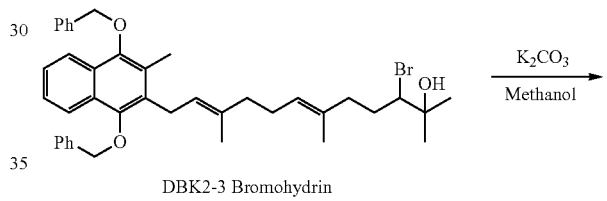

Dibenzyl ether of Vitamin K2-3 bromohydrin was added to potassium carbonate solution dissolved in methanol. After completion of the reaction, methanol was distilled off followed by extraction with ethyl acetate solvent to yield Dibenzyl ether Vitamin K2-3 epoxide.

Step 8: Preparation of Dibenzyl Ether Vitamin K2-3 Alcohol

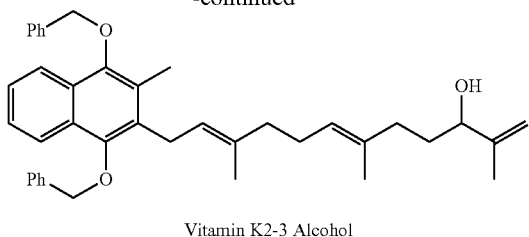

Vitamin K2-3 Alcohol

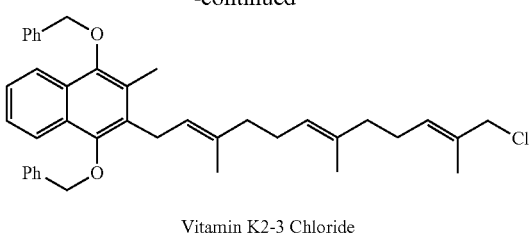

Vitamin K2-3 Chloride

The epoxide was dissolved in Toluene followed by the addition of aluminium iso-propoxide and was heated to reflux. After completion of reaction toluene was distilled off followed by ethyl acetate extraction and washed with potassium sodium tartrate solution. Stripping off the solvent yielded Dibenzyl ether Vitamin K2-3 alcohol.

Step 9: Preparation of Dibenzyl Ether Vitamin K2-3 Chloride

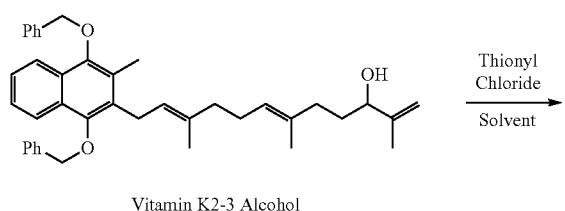

Vitamin K2-3 Alcohol

Thionyl Chloride / Solvent

The Dibenzyl ether Vitamin K2-3 alcohol was dissolved in Hexane and cooled to 10° C. followed by thionyl chloride addition. After completion of the reaction, it was neutralized with sodium bicarbonate solution followed by stripping off the solvent.

Step 10: Preparation of Geranyl Geranyl Phenyl Sulphonate:

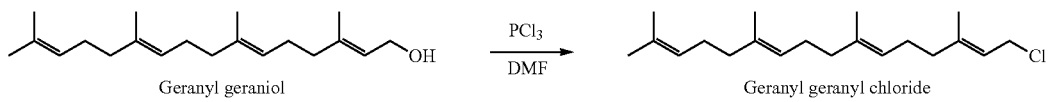

Geraniol geraniol → Geranyl geranyl chloride

Benzene sulfinic acid sodium salt | THF

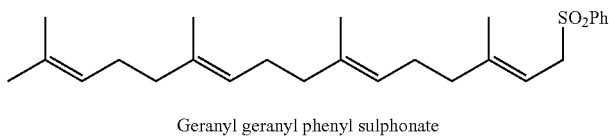

Geranyl geranyl phenyl sulphonate

Geranyl Geraniol was dissolved in DMF and cooled to 5-10° C. PCl$_3$ was added. After completion of the reaction, unreacted PCl$_3$ was neutralized with sodium bicarbonate followed by extraction with hexane to yield the chloride intermediate which was further reacted with sodium benzene sulphonate to yield Geranyl geranyl phenyl sulphonate.

Step 11 A: Preparation of Dibenzyl Ether Vitamin K2-7 SO2Ph (where SO$_2$Ph is at 16$^{th}$ Position)

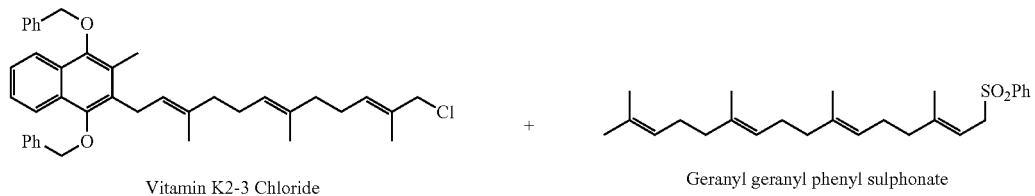

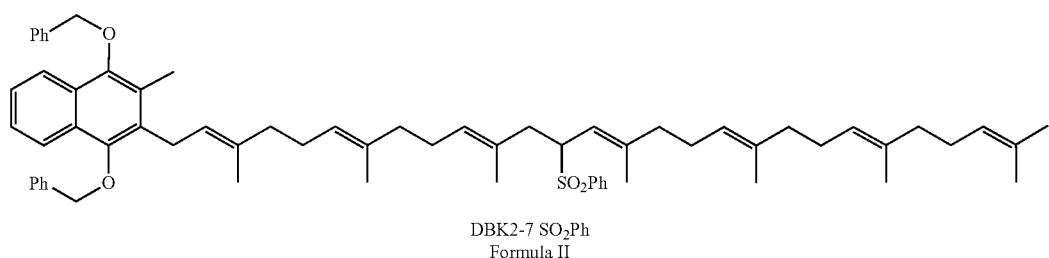

DBK2-7 SO$_2$Ph
Formula II

The compound of 16 sulphophenyl 1,4 dibenzyl ether of Vitamin K2-7 provided by Formula II is a novel compound of the invention.

Step 11B: Preparation of Dibenzyl Ether Vitamin K2-7 SO2Ph (where SO2Ph is at 21st Position)

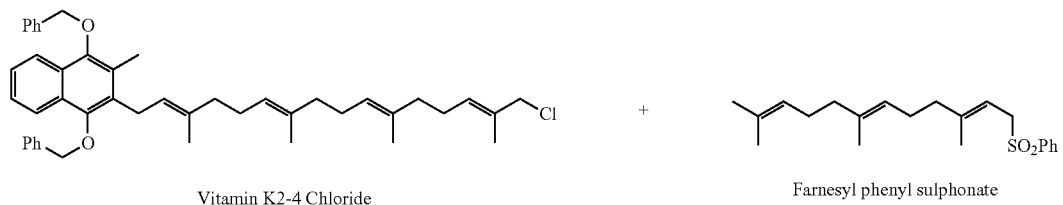

The compound of 21 sulphophenyl 1,4 dibenzyl ether of Vitamin K2-7 provided by Formula III is a novel compound of the invention.

Geranyl geranyl phenyl sulphonate was dissolved in Toluene followed by KOH addition and PTC. To the reaction

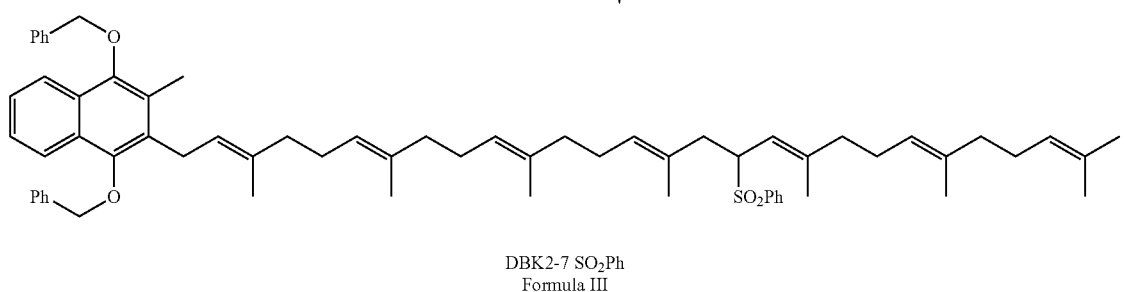

DBK2-7 SO$_2$Ph
Formula III mass was added Dibenzyl ether Vitamin K2-3 chloride drop wise. After completion of the reaction the product was isolated from the organic layer.

Step 12: Preparation of Vitamin K2-7

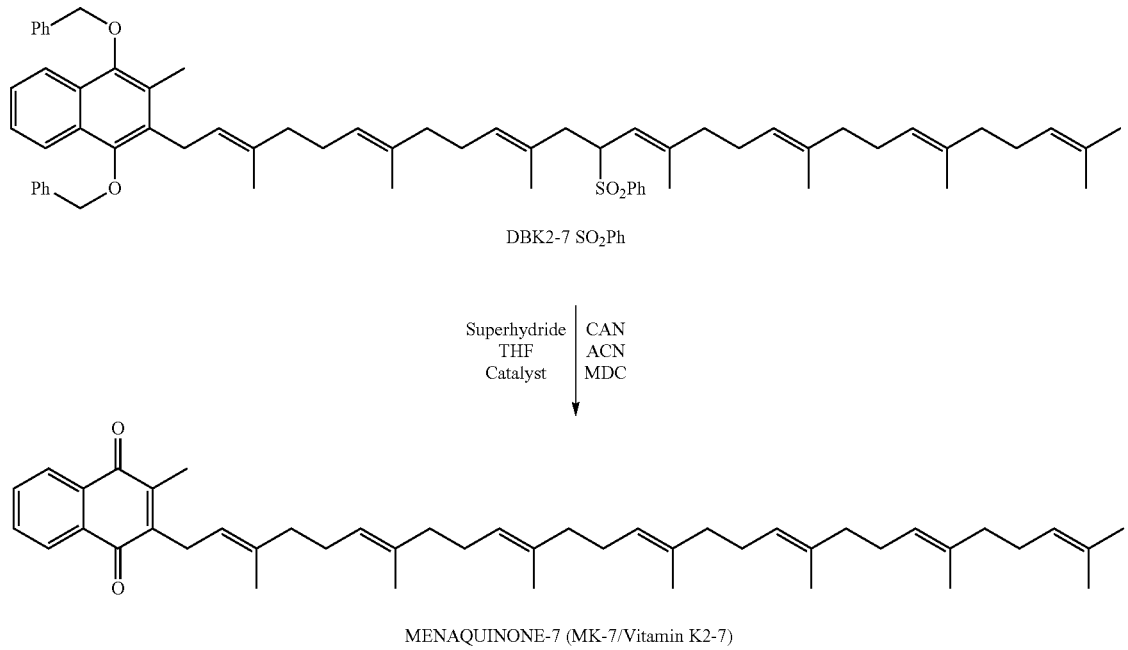

DBK2-7 SO₂Ph

MENAQUINONE-7 (MK-7/Vitamin K2-7)

Desulphonation and Debenzylation were carried out sequentially with Super hydride and Ceric ammonium nitrate.

The following examples illustrate the various aspects of the disclosure but do not limit the scope of the disclosure in any manner.

Example 1

Preparation of Cyclopentadiene Menadione Adduct

Cyclopentadiene (freshly prepared) 3.2 g, 8.4 mmol was added with stirring to 2-Methyl naphthoquinone 3.4 g, 9.8 mmol solubilised in CTAB (Cetyl Trimethyl Ammonium Bromide) prepared by dissolving 0.03 g, 0.0823 mmol in 100 ml distilled water. The reaction mixture was stirred for 3 hours at room temperature (~30° C.). It was extracted with ether (25 ml×3), the organic layer was washed with water (20 ml×2), brine (20 ml) and dried over anhydrous sodium sulphate. Removal of solvent followed by recrystallization of the residue gave 4.04 g, cyclopentadiene menadione adduct, (86% yield).

$^1$H NMR and $^{13}$C NMR characterization of cyclopentadiene menadione adduct. $^1$H NMR (400 MHz, CDCl3) δ 7.92-7.94 (m, 2H), 7.81-7.85 (m, 2H), 6.02-6.05 (m, 1H), 5.88-5.91 (m, 1H), 3.41 (s, 1H), 3.16 (d, 1H), 3.08 (s, 1H), 1.80-1.82 (dd, 1H), 1.51 (s, 3H), 1.41-1.43 (dd, 1H). $^{13}$C NMR (400 MHz, CDCI3) δ 200.63, 197.13, 137.96, 135.06, 134.74. 134.41, 134.28, 126.64, 126.12, 57.03, 53.61, 53.14, 48.92, 46.10, 40.13, 26.28.

The reaction was carried out under similar conditions without CTAB, no product formation was observed.

Example 2

2.a. Preparation of Geranyl Chloride 15 ml N, N-dimethyl formamide was cooled to 5-10° C. 1.02 g (0.0075 mol) of phosphorus trichloride at 5-10° C.
was slowly added over 10 minutes. Reaction mass was stirred for additional 20 minutes at the same temperature. 1.54 g (~0.01 mole) of geraniol was dissolved in 1.9 ml N, N-dimethyl formamide and added to the above solution over 10 minutes at 5-10° C. Reaction mass was stirred for additional 2-3 hours at the same temperature and the progress of the reaction was monitored by TLC. After the completion of reaction, sodium bicarbonate was added to adjust pH to 8 and the reaction mass was extracted with hexane. Hexane layer was washed with water followed by brine and dried over anhydrous sodium sulphate. Hexane was distilled under vacuum to give 1.56 g of geranyl chloride as yellow colored oil.

$^1$H NMR and $^{13}$C NMR characterization of geranyl chloride: $^1$H NMR (400 MHz, CDCl$_3$) δ 5.46 (m, 1H), 5.1 (m, 1H), 4.12 (dd, 2H), 2.06-2.13 (m, 4H), 1.75 (s, 3H), 1.70 (s, 3H), 1.62 (s, 3H). $^{13}$C NMR (400 MHz, CDCI$_3$) δ 142.68, 131.91, 123.59, 120.32, 41.09, 39.45, 26.22, 25.66, 17.67, 16.07.

2.b. Preparation of Farnesyl Chloride 15 ml N, N-dimethyl formamide was cooled to 5-10° C. 1.02 g (0.0075 mol) of phosphorus trichloride was slowly added over 10 minutes at 5-10° C. Reaction mass was stirred for additional 20 minutes at the same temperature. 2.22 g (~0.01 mole) farnesol was dissolved in 2.7 ml N, N-dimethyl formamide and added to the above solution in 10 minutes at 5-10° C. Reaction mass was stirred for additional 3 hours at the same temperature and the progress of the reaction was monitored by TLC. After the completion of reaction, sodium bicarbonate was added to adjust the pH to 8 and the reaction mass was extracted with hexane. Hexane layer was washed with water followed by brine and dried over anhydrous sodium sulphate. Hexane was distilled under vacuum to yield 2.3 g of farnesyl chloride as dark red coloured oil.

$^1$H NMR and $^{13}$C NMR characterization of farnesyl chloride: $^1$H NMR (400 MHz, CDCl$_3$) δ 5.43 (m, 1H), 5.20 (m, 2H), 4.05 (dd, 2H), 2.00 (m, 8H), 1.71 (s, 12H). $^{13}$C NMR (400 MHz, CDCl$_3$) δ 138, 132.5, 125.2, 123.5, 122.7, 40.7, 39.8, 39, 26.7, 26.4, 25.6, 19.6, 17.5, 16.7.

2.c. Preparation of Geranyl Geranyl Chloride 15 ml N, N-dimethyl formamide was cooled to 5-10° C. 1.02 g (0.0075 mol) of phosphorus trichloride was slowly added over 10 minutes at 5-10° C. Reaction mass was stirred for additional 20 minutes at the same temperature. 2.905 g (~0.01 mole) Geranyl geraniol dissolved in 3.5 ml N, N-dimethyl formamide and added to the above solution over 10 minutes at 5-10° C. Reaction mass was stirred for additional 3 hours at the same temperature and the progress of the reaction was monitored by TLC. After the completion of the reaction sodium bicarbonate was added to adjust pH to 8 and the reaction mass was extracted with hexane. Hexane layer was washed with water followed by brine and dried over anhydrous sodium sulphate. Hexane was distilled under vacuum to yield 2.95 g Geranyl geranyl chloride as dark red coloured oil.

$^1$H NMR and $^{13}$C NMR characterization of Geranyl geranyl chloride: $^1$H NMR (400 MHz, CDCl$_3$) δ 5.46 (m, 1H), 5.11 (m, 3H), 4.11 (d, 2H), 2.07-2.14 (m, 8H), 1.97-2.02 (m, 4H), 1.75 (s, 3H), 1.7 (s, 3H), 1.62 (s, 9H). $^{13}$C NMR (400 MHz, CDCl$_3$) δ 142.71, 135.59, 134.94, 131.22, 124.40, 124.19, 123.47, 120.35, 41.09, 39.75, 39.70, 39.47, 26.78, 26.61, 26.13, 25.72, 17.69, 16.1, 16.05, 16.01.

2.d. Preparation of Solanesyl Chloride 15 ml N, N-dimethyl formamide was cooled to 5-10° C. 1.02 g (0.0075 mol) of phosphorus trichloride was slowly added over 10 minutes at 5-10° C. Reaction mass was stirred for additional 20 minutes at the same temperature. 6.31 g (~0.01 mole) of solanesol was dissolved in 25 ml N, N-dimethyl formamide and added to the above solution in 10 minutes at 5-10° C. Reaction mass was stirred for additional 2-3 hours at the same temperature and the progress of the reaction was monitored by TLC. After completion of the reaction, sodium bicarbonate was added to adjust the pH to 8 and the reaction mass was extracted with ethyl acetate. Ethyl acetate layer was washed with water followed by brine and dried over anhydrous sodium sulphate. Ethyl acetate was distilled under vacuum to give 5.4 g of Solanesyl chloride as yellow coloured oil.

$^1$H NMR and $^{13}$C NMR characterization of Solanesyl chloride:

$^1$H NMR (400 MHz, CDCl$_3$) δ 5.47 (m, 1H), 5.12 (m, 8H), 4.11 (d, 2H), 2.07-2.10 (m, 18H), 2.0 (m, 14H), 1.75 (s, 3H), 1.70 (s, 3H), 1.62 (s, 24H). $^{13}$C NMR (400 MHz, CDCl$_3$) δ 142.68, 135.60, 134.97, 134.88, 134.86, 134.84, 131.18, 124.45, 124.29, 124.19, 123.46, 120.37, 41.06, 39.77, 39.48, 26.79, 26.72, 26.69, 26.65, 26.14, 25.73, 17.70, 16.11, 16.04.

Example 3

3.1. Preparation of Vitamin K2-2

3.1.1. Preparation of Vitamin K2-2 Cyclopentadiene Adduct

In a mixture of 1 ml of t-butanol and 4 ml of toluene, 2.24 g (0.02 mol) of potassium t-butoxide was added. 2.38 g (0.01 mol) of cyclopentadiene menadione adduct, dissolved in mixture of 1.46 ml of t-butanol and 5.83 ml of toluene, was added to the above reaction mass at 30° C. in 10 minutes. Reaction mass was stirred for 10 minutes. 2.6 g (0.015 mol) of geranyl chloride, dissolved in mixture of 0.4 ml of t-butanol and 1.6 ml of toluene was added to the above reaction mass at 30° C. over 10 minutes and stirred for 1 hour at the same temperature and the progress of the reaction was monitored by TLC. After completion of the reaction, the reaction mass was quenched in distilled water and pH was adjusted to 5-6 using 1N HCl. Layers were separated and toluene layer was washed with water followed by brine and dried over anhydrous sodium sulphate.

3.1.2. Preparation of Vitamin K2-2

Toluene layer was refluxed for 30 minutes to obtain Vitamin K2-2 by retro Diels-alder reaction. Toluene was distilled under vacuum to give 4.1 g of crude K2-2 as dark red thick oil.

3.2. Preparation of Vitamin K2-3

3.2.1. Preparation of Vitamin K2-3 Cyclopentadiene Adduct

In a mixture of 1 ml of t-butanol and 4 ml of toluene, 2.24 g (0.02 mol) of potassium t-butoxide was added. 2.38 g (0.01 mol) of cyclopentadiene menadione adduct, dissolved in mixture of 1.46 ml of t-butanol and 5.83 ml of toluene, was added to the above reaction mass at 30° C. over 10 minutes. Reaction mass was stirred for 10 minutes. 3.6 g (0.015 mol) of farnesyl chloride, dissolved in mixture of 0.4 ml of t-butanol and 1.6 ml of toluene, was added to the above reaction mass at 30° C. over 10 minutes and stirred for 1 hour at same temperature. The reaction mass was quenched in distilled water and the pH was adjusted to 5-6 using 1N HCl. The layers were separated. Toluene layer was washed with water followed by brine and dried over anhydrous sodium sulphate.

In this experiment it was observed that the solvent composition had as significant effect on the yield of vitamin K2 and especially the impurity content as shown in the table below, which also shows the time required to the absence of the starting material.

| | | RATIO OF IMPURITY TO K2 PRODUCT* | | | | |
| --- | --- | --- | --- | --- | --- | --- |
| | | K2-3 (Impurity:Product) | | | K2-4 (Impurity:Product) | K2-9 (Impurity:Product) |
| Sr. No | % T-butanol in Toluene | 20° C. | 30° C. | 40° C. | 30° C. | 30° C. |
| 1 | 0% | 1:8.72 (24 hr) | 1:11.03 (2 hr) | 1:11.68 (2 hr) | 1:10.34 (2 hr) | — |
| 2 | 10.7% | 1:17.8 (24 hr) | 1:17.07 (1 hr) | 1:15.56 (1 hr) | 1:16.13 (2 hr) | — |
| 3 | 20% | 1:15.9 (24 hr) | 1:18.07 (1 hr) | 1:14.04 (1 hr) | 1:15.64 (2 hr) | 1:11.1 (1 hr) |
| 4 | 31% | 1:17.2 (24 hr) | 1:17.07 (2 hr) | 1:14.55 (2 hr) | 1:9.87 (3 hr) | 1:7.42 (5 hr) |
| 5 | 41% | 1:11.42 (24 hr) | 1:11.2 (3 hr) | 1:9.9 (2 hr) | 1:8.97 (3 hr) | 1:6.29 (5 hr) |
| 6 | 50% | 1:8.6 (24 hr) | 1:13.91 (3 hr) | 1:9.95 (2 hr) | 1:6.07 (5 hr) | — |

-continued

RATIO OF IMPURITY TO K2 PRODUCT*

| Sr. No | % T-butanol in Toluene | K2-3 (Impurity:Product) 20° C. | K2-3 (Impurity:Product) 30° C. | K2-3 (Impurity:Product) 40° C. | K2-4 (Impurity:Product) 30° C. | K2-9 (Impurity:Product) 30° C. |
|---|---|---|---|---|---|---|
| 7 | 60% | 1:8.65 (24 hr) | 1:7.56 (4 hr) | 1:9.12 (2 hr) | 1:3.2 (5 hr) | 1:5.15 (5 hr) |
| 8 | 80% | 1:8.62 (24 hr) | 1:8.89 (1 hr) | 1:11.35 (1 hr) | 1:12.9 (2 hr) | — |
| 9 | 100% | 1:7.83 (24 hr) | 1:8.64 (2 hr) | 1:9 (1 hr) | 1:10.22 (2 hr) | — |

3.2.2 Preparation of Vitamin K2-3

Toluene layer was refluxed for 30 minutes to yield Vitamin K2-3 by retro Diels-alder reaction. Toluene was distilled under vacuum to give 5 g of crude K2-3 as dark red thick oil.

$^1$H NMR and $^{13}$C NMR characterization of Vitamin K2-3: $^1$H NMR (400 MHz, CDCl$_3$) δ 7.92 (m, 2H), 7.8 (m, 2H), 4.97 (m, 3H), 3.28 (d, 2H), 2.08 (s, 3H), 1.77-2.0 (m, 8H), 1.73 (s, 3H), 1.57 (s, 3H), 1.48 (d, 6H). $^{13}$C NMR (400 MHz, CDCl$_3$) δ 184.42, 183.59, 145.14, 142.73, 136.24, 134.30, 133.64, 133.62, 131.42, 130.40, 125.75, 125.67, 123.91, 123.49, 119.35, 40.15, 39.73, 38.90, 26.09, 25.68, 25.40, 25.32, 17.28, 15.75, 15.67, 12.19.

3.3 Preparation of Vitamin K2-4

3.3.1. Preparation of Vitamin K2-4 Adduct

In a mixture of 1 ml of t-butanol and 4 ml of toluene, 2.24 g (0.02 mol) of potassium t-butoxide was added. 2.38 g (0.01 mol) of cyclopentadiene menadione adduct, dissolved in mixture of 1.46 ml of t-butanol and 5.83 ml of toluene, was added to the above reaction mass at 30° C. over 10 minutes. Reaction mass was stirred for 10 minutes. 4.63 g (0.015 mol) of Geranyl geranyl chloride, dissolved in mixture of 0.4 ml of t-butanol and 1.6 ml of toluene, was added to the above reaction mass at 30° C. over 10 minutes and stirred for 1 hour at same temperature. Reaction mass was quenched in distilled water and the pH was adjusted to 5-6 using 1N HCl. Layers were separated and toluene layer was washed with water followed by brine and dried over anhydrous sodium sulphate.

3.3.2 Preparation of Vitamin K2-4

Toluene layer from the above experiment was refluxed for 30 minutes to synthesize Vitamin K2-4 by retro Diels-alder reaction. Toluene was distilled under vacuum to yield 6.3 g of crude K2-4 as dark red thick oil.

$^1$H NMR and $^{13}$C NMR characterization of Vitamin K2-4: $^1$H NMR (400 MHz, DMSO) δ 7.98 (m, 2H), 7.82 (m, 2H), 5.01 (m, 4H), 3.28 (m, 2H), 2.09 (s, 3H), 1.82-2.04 (m, 12H), 1.78 (s, 3H), 1.67 (s, 3H), 1.57 (s, 3H), 1.48 (s, 3H), 1.45 (s, 3H). $^{13}$C NMR (400 MHz, DMSO) δ 185.05, 184.21, 145.71, 143.30, 136.71, 134.77, 134.63, 134.25, 134.23, 131.98, 131.97, 131.00, 126.31, 126.23, 124.54, 124.21, 124.09, 119.91, 40.62, 40.41, 40.20, 26.62, 26.37, 26.19, 25.92, 25.89, 17.93, 16.56, 16.22, 16.10, 12.77.

3.4 Preparation of Vitamin K2-9

3.4.1 Preparation of Vitamin K2-9 Adduct

In a mixture of 1 ml of t-butanol and 4 ml of toluene, 2.24 g (0.02 mol) of potassium t-butoxide added. 2.38 g (0.01 mol) of cyclopentadiene menadione adduct, dissolved in mixture of 1.46 ml of t-butanol and 5.83 ml of toluene was added to the reaction mass at 30° C., over 10 minutes. Reaction mass was stirred for 10 minutes. 9.7 g (0.015 mol) of solanesyl chloride, dissolved in mixture of 0.4 ml of t-butanol and 1.6 ml of toluene was added to the above reaction mass at 30° C. over 10 minutes and stirred for 1 hour at same temperature. Reaction mass was quenched in distilled water and pH was adjusted to 5-6 using 1N HCl. Layers were separated and toluene layer was washed with water followed by brine and dried over anhydrous sodium sulphate.

3.4.2 Preparation of K2-9

Toluene layer was refluxed for 30 minutes to obtain Vitamin K2-9 by retro Diels-alder reaction Toluene was distilled under vacuum to give 11 g of crude Vitamin K2-9 as dark red thick oil.

H NMR characterization of Vitamin K2-9: 1H NMR (400 MHz, CDCl$_3$) δ 8.11 (m, 2H), 7.71 (m, 2H), 5.04-5.14 (m, 9H), 3.38 (d, 2H), 2.06-2.08 (m, 8H), 1.99-2.01 (m, 8H), 1.81 (s, 3H), 1.70 (s, 3H), 1.58-1.61 (m, 27H).

Example 4

Following Examples Illustrate the Chain Extension Technique when the Prenyl Compound Corresponding to the Vitamin K2 to be Synthesized, is not Readily Available 4.1 Preparation of Dibenzyl Ether of Vitamin K2-3

6.96 g (0.04 mol) of sodium dithionite was dissolved in 16.5 ml distilled water. To this solution 0.02 g tetrabutylammonium bromide was added and the reaction mass was cooled to 15° C. 3.76 g (0.01 mol). Vitamin K2-3 dissolved in 20 ml tetrahydrofuran was added to the above solution over 30 minutes under inert atmosphere. The reaction mass was stirred further for 60 minutes at 20-25° C. and neutralized with sodium bicarbonate. It was cooled to 5° C. and 11.2 g of 50% w/w aqueous potassium hydroxide solution was added. This was followed by the addition of 3.79 g (0.03 mol) benzyl chloride in 4 ml tetrahydrofuran in a dropwise manner over 30-40 minutes. The reaction mass was allowed to stir for 20 hours at room temperature. Tetrahydrofuran was distilled under vacuum and residue was extracted with ethyl acetate. Ethyl acetate layer was washed with water followed by brine and dried over anhydrous sodium sulphate. Ethyl acetate was distilled under vacuum to give 5.58 g, Dibenzyl ether Vitamin K2-3 of 90% purity.

$^1$H NMR and $^{13}$C NMR characterization of DBK2-3: $^1$H NMR (400 MHz, CDCl$_3$) δ 8.03 (s, 1H), 7.0-7.55 (m, 13H), 4.8-5.0 (m, 4H), 3.4-3.6 (d, 2H), 2.33 (s, 3H), 1.83-2.0 (m, 10H), 1.69 (s, 3H), 1.54 (s, 3H), 1.48 (s, 3H), 1.44 (s, 3H). $^{13}$C NMR (400 MHz, CDCl$_3$) δ 148.47, 148.12, 138.21, 137.33, 137.28, 135.19, 134.33, 130.80, 130.42, 128.77, 128.37, 127.89, 127.78, 127.54, 127.17, 127.02, 126.95, 126.73, 125.66, 125.55, 123.98, 123.64, 122.59, 122.02, 121.87, 75.98, 75.11, 40.19, 39.98, 39.77, 38.94, 35.18, 26.14, 26.05, 25.81, 25.30, 17.29, 16.01, 15.67, 12.40.

4.2 Preparation of Dibenzyl Ether of Vitamin K2-4

6.96 g (0.04 mol) of sodium dithionite was dissolved in 16.5 ml distilled water. To this solution 0.02 g tetra butylammonium bromide was added and the reaction mass was cooled to 15° C. 4.44 g (0.01 mol) Vitamin K2-4 synthesized as discussed in example 3.3 was dissolved in 20 ml tetrahydrofuran and was added to the above solution over 30 minutes under inert atmosphere. The reaction mass was stirred further for 60 minutes at 20-25° C. and neutralized with sodium bicarbonate. It was cooled to 5° C. and 11.2 g of 50% w/w potassium hydroxide aqueous solution was added followed by addition of 3.79 g (0.03 mole) benzyl chloride in 4 ml tetrahydrofuran in a dropwise manner in 30-40 minutes. The reaction mass was stirred for 20 hours at room temperature. Tetrahydrofuran was distilled under vacuum and residue was extracted with ethyl acetate. Ethyl acetate layer was washed with water followed by brine and dried over anhydrous sodium sulphate. Ethyl acetate was distilled under vacuum to give 7 g, 87% pure Dibenzyl ether of Vitamin K2-4 as oil.

Example 5

5.1 Preparation of Dibenzyl Ether Vitamin K2-3 Bromohydrin 5.58 g (~0.01 mole) Dibenzyl vitamin K2-3 was dissolved in 28 ml tetrahydrofuran and cooled to −5 to 0° C. 6-10 ml water was added dropwise until Dibenzyl vitamin K2-3 turned into a turbid solution. 1-3 ml tetrahydrofuran was added to the reaction mass when a clear solution was formed. 2.13 g (0.012 mole) N-Bromo succinimide was added in small portions at a time to the above reaction mass over 30 minutes. Reaction mass was stirred for 4 hours and was quenched with sodium thiosulfate solution at −5 to 0° C. Tetrahydrofuran was distilled under vacuum and residue was extracted in ethyl acetate. Ethyl acetate layer was washed with distilled water followed by brine and dried over anhydrous sodium sulfate. Ethyl acetate was distilled under vacuum to give 5.89 g of crude Dibenzyl vitamin K2-3 Bromohydrin as oil. Crude product was purified by column chromatography in mixture of hexane and ethyl acetate to yield 4 g Dibenzyl vitamin K2-3 Bromohydrin as light yellow oil.

5.2 Preparation of Dibenzyl Ether Vitamin K2-4 Bromohydrin 6.27 g (~0.01 mole) Dibenzyl ether vitamin K2-4 was dissolved in 31 ml tetrahydrofuran and cooled to −5 to 0° C. 8-12 ml water was added dropwise when Dibenzyl ether vitamin K2-4 turned into a turbid solution. 2-3 ml tetrahydrofuran was added to reaction mass when a clear solution was formed. 2.13 g (0.012 mole) N-Bromo succinimide was added in small portions at a time to the above reaction mass over 30 minutes. Reaction mass was stirred for 4 hours and was quenched with sodium thiosulfate solution at −5 to 0° C. Tetrahydrofuran was distilled under vacuum and residue was extracted in ethyl acetate. Ethyl acetate layer was washed with distilled water followed by brine and dried over anhydrous sodium sulfate. Ethyl acetate was distilled under vacuum to yield 6.5 g of crude Dibenzyl ether vitamin K2-4 Bromohydrin as reddish oil. Crude product was purified by column chromatography in mixture of hexane and ethyl acetate to yield 4.5 g Dibenzyl ether vitamin K2-4 Bromohydrin as light yellow oil.

Example 6

6.1 Preparation of Dibenzyl Ether Vitamin K2-3 Epoxide 2.07 g (0.015 mole) of potassium carbonate was added in 60 ml methanol to yield a turbid solution. 6.55 g (~0.01 mole) Dibenzyl vitamin K2-3 Bromohydrin was dissolved in 20 ml methanol and was added to the above solution over 10 minutes while stirring. Reaction mass was stirred for 16 hours at room temperature. Methanol was distilled under vacuum and residue was extracted in ethyl acetate. Ethyl acetate layer was washed with water followed by brine and dried over anhydrous sodium sulfate. Ethyl acetate was distilled under vacuum to yield 5.74 g Dibenzyl ether vitamin K2-3 Epoxide as yellow oil 6.2 Preparation of Dibenzyl Ether Vitamin K2-4 Epoxide 2.07 g (0.015 mole) of potassium carbonate was added in 60 ml methanol to yield a turbid solution. 7.23 g (~0.01 mole) Dibenzyl ether vitamin K2-4 Bromohydrin was dissolved in 21 ml methanol and was added to the above solution over 10 minutes while stirring. Reaction mass was stirred for 16 hours at room temperature. Methanol was distilled under vacuum and residue was extracted in ethyl acetate. Ethyl acetate layer was washed with water followed by brine and dried over anhydrous sodium sulfate. Ethyl acetate was distilled under vacuum to yield 6.42 g Dibenzyl ether vitamin K2-4 Epoxide as yellow oil.

Example 7

7.1 Preparation of Dibenzyl Ether Vitamin K2-4 Alcohol 6.42 g (~0.01 mole) Dibenzyl ether vitamin K2-4 Epoxide was dissolved in 64.2 ml toluene. 10.21 g (0.05 mole) aluminium iso-propoxide was added to the above solution at room temperature. Reaction mass was refluxed for 20-24 hours. and then brought to room temperature. Toluene was distilled under vacuum and residue obtained was dissolved in ethyl acetate and washed with saturated solution of potassium sodium tartarate followed by water followed by brine and dried over anhydrous sodium sulfate. Ethyl acetate was distilled under vacuum to yield 6.42 g of crude Dibenzyl ether vitamin K2-4 Alcohol as yellow oil. Crude product was purified by column chromatography to yield 4.3 g, Dibenzyl ether vitamin K2-4 Alcohol, of 90% purity as light yellow oil.

7.2 Preparation of Dibenzyl Ether Vitamin K2-3 Alcohol 5.74 g (~0.01 mole) Dibenzyl K2-3 Epoxide was dissolved in 57.4 ml toluene. 10.21 g (0.05 mole) aluminium iso-propoxide was added to the above solution. Reaction mass was refluxed for 20-24 hours. and then brought to room temperature. Toluene was distilled under vacuum and residue obtained was dissolved in ethyl acetate and washed with saturated solution of potassium sodium tartarate followed by water followed by brine and dried over anhydrous sodium sulfate. Ethyl acetate was distilled under vacuum to yield 5.74 g of crude Dibenzyl ether vitamin K2-3 Alcohol as yellow oil. Crude product was purified by column chromatography to yield 3.9 g, Dibenzyl ether vitamin K2-3 Alcohol, of 90% purity as light yellow oil.

Example 8

8.1 Preparation of Dibenzyl Ether Vitamin K2-3 Chloride 5.74 g (0.01 mol) Dibenzyl ether Vitamin K2-3 alcohol was dissolved in 57.4 ml hexane and cooled to 10° C. 1.31 g (0.011 mol) of thionyl chloride in 57.4 ml hexane was added slowly over 30 minutes to the above solution under stirring. Reaction mass was allowed to attain room temperature and stirred overnight, cooled to 15° C. and pH was adjusted to 6-7 using saturated solution of sodium bicarbonate. Aqueous and organic layers were separated and organic layer was washed with water followed by brine and dried over anhydrous sodium sulphate. Hexane was distilled under vacuum to yield 5.74 g, 97% yield, Dibenzyl ether Vitamin K2-3 Chloride as oil.

8.2 Preparation of Dibenzyl Ether Vitamin K2-4 Chloride 6.2 g (0.009 mol) of Dibenzyl ether Vitamin K2-4 Alcohol was dissolved in 62 ml hexane and cooled to 10° C. 1.72 g (0.015 mol) of thionyl chloride in 10 ml of hexane was added slowly to the above solution under stirring over 30 minutes. Reaction mass was allowed to attain room temperature and stirred overnight, cooled to 15° C. and pH was adjusted to 6-7 using saturated solution of sodium bicarbonate. Aqueous and organic layers were separated and organic layer was washed with water followed by brine and dried over anhydrous sodium sulphate. Hexane was distilled under vacuum to yield 5.5 g, of Dibenzyl ether Vitamin K2-4 Chloride as oil. Yield 97%.

Example 9

9A. Preparation of Farnesyl Phenyl Sulphonate
9.A.1. Stage 1:
15 ml N, N-dimethyl formamide was cooled to 5-10° C. 1.02 g (0.0075 mol) of phosphorus trichloride was slowly added in 10 minutes. Reaction mass was stirred for additional 20 minutes at the same temperature. 2.22 g (~0.01 mole) farnesol was dissolved in 2.7 ml N, N-dimethyl formamide and added to the above solution in 10 minutes. Reaction mass was stirred for additional 3 hours at the same temperature and then quenched with sodium bicarbonate to adjust pH to 8 and extracted with hexane. Hexane layer was washed with water followed by brine and dried over anhydrous sodium sulphate. Hexane was distilled under vacuum to yield 2.3 g of farnesyl chloride as dark red colored oil.
9.A.2 Stage 2
1.97 g (0.012 mol) of sodium benzene sulphonate in 6.8 ml of N, N-dimethyl formamide was cooled to 10-15° C. and 2.4 g (~0.01 mole) of farnesyl chloride dissolved in 2.9 ml of N, N-dimethyl formamide, was added to the above solution over 10 minutes at 10-15° C. Reaction mass was brought to room temperature and stirred for 15 hours, was quenched with distilled water and extracted in hexane. Hexane layer was washed with water followed by brine and dried over anhydrous sodium sulphate. Hexane was distilled under vacuum to give 3.4 g of crude farnesyl phenyl sulphonate as dark red colour oil. Crude product was purified by column chromatography in mixture of hexane and ethyl acetate or by crystallization in methanol to give 2.7 g farnesyl phenyl sulphonate, 97% pure as colorless oil.
9.B. Preparation of Geranyl Geranyl Phenyl Sulphonate
9.B.1 Stage 1:
15 ml N, N-dimethyl formamide was cooled to 5-10° C. 1.02 g (0.0075 mol) of phosphorus trichloride was slowly added over 10 minutes at 5-10° C. Reaction mass was stirred for additional 20 minutes at the same temperature. 2.905 g (~0.01 mole) Geranyl geraniol was dissolved in 3.5 ml N, N-dimethyl formamide and was added to the above solution over 10 minutes at 5-10° C. Reaction mass was stirred for additional 3 hours at the same temperature and then quenched with sodium bicarbonate to adjust pH to 8 and extracted with hexane. Hexane layer was washed with water followed by brine and dried over anhydrous sulphate. Hexane was distilled under vacuum to yield 2.95 g Geranyl geranyl chloride as dark red coloured oil.
9.B.2 Stage 2:
1.97 g (0.012 mol) of sodium benzene sulphonate in 6.8 ml of N, N-dimethyl formamide was cooled to 10-15° C. 3.09 g (~0.01 mole) of Geranyl geranyl chloride dissolved in 3.8 ml of N, N-dimethyl formamide, was added to the above solution in 10 minutes at 10-15° C. Reaction mass was brought to room temperature and stirred for 15 hours, quenched with distilled water and extracted in hexane. Hexane layer was washed with water followed by brine and dried over anhydrous sodium sulphate. Hexane was distilled under vacuum to give 3.7 g of crude geranyl geranyl phenyl sulphonate as dark red coloured oil. Crude product was purified by column chromatography in mixture of hexane and ethyl acetate or by crystallization in methanol to yield 2.8 g Geranyl geranyl phenyl sulphonate, as colourless oil of 98% purity.

$^1$H NMR and $^{13}$C NMR characterization data for Geranyl geranyl phenyl sulphonate: $^1$H NMR (400 MHz, CDCl$_3$) δ 7.86 (m, 2H), 7.64 (m, 1H), 7.54 (m, 2H), 5.22 (m, 1H), 5.12 (m, 3H), 3.82 (m, 2H), 1.95-2.0 (m, 12H), 1.68 (s, 3H), 1.60 (s, 9H), 1.30 (s, 3H). $^{13}$C NMR (400 MHz, CDCl$_3$) δ 146.42, 138.61, 135.68, 134.98, 133.53, 131.22, 128.94, 128.55, 124.36, 124.09, 123.34, 110.30, 77.46, 77.14, 76.82, 56.06, 39.71, 39.68, 26.74, 26.57, 26.17, 25.71, 17.69, 16.15, 16.01.

Example 10

Preparation of Dibenzyl Ether Vitamin K2 SO2Ph

10. A. Preparation of Dibenzyl Ether Vitamin K2-6 SO2Ph 3.47 g (0.01 mol) Farnesyl phenyl sulphonate and 7.12 g (0.019 mol) Dibenzyl ether vitamin K2-3 Chloride were dissolved in 82.8 ml toluene. 60% w/w 41.4 g aqueous solution of potassium hydroxide was added followed by 0.414 g of tetra butyl ammonium bromide and 0.207 g 18 crown 6 (1,4,7,10,13,16-hexaoxacyclooctadecane) at 30° C. Reaction mass was stirred vigorously overnight at same temperature. Layers were separated. Toluene layer was washed with distilled water followed by 5% acetic acid, distilled water, brine and dried over anhydrous sodium sulphate. Toluene was distilled under vacuum to yield 12 g of crude Dibenzyl K2-6 Phenyl Sulphonate as dark red color oil. Crude product was purified by column chromatography in mixture of hexane and ethyl acetate to give 8.5 g Dibenzyl ether of Vitamin K2-6 Phenyl Sulphonate, as light-yellow oil of 96% purity.

10.B. Preparation of Dibenzyl Ether Vitamin K2-7 SO$_2$Ph
4.14 g (0.01 mol) Geranyl geranyl phenyl sulphonate and 7.2 g (0.012 mol) Dibenzyl Vitamin K2-3-Chloride were dissolved in 82.8 ml toluene. 60% w/w 41.4 g aqueous solution of potassium hydroxide was added followed by 0.414 g of tetrabutyl ammonium bromide and 0.207 g 18 crown 6 at 30° C. Reaction mass was stirred vigorously overnight at same temperature. Layers were separated. Toluene layer was washed with distilled water followed by 5% acetic acid, distilled water, brine and dried over anhydrous sodium sulphate. Toluene was distilled under vacuum to yield 12 g of crude Dibenzyl ether vitamin K2-7 Phenyl Sulphonate as dark red coloured oil. Crude product was purified by column chromatography using a mixture of hexane and ethyl acetate to give 8.2 g Dibenzyl K2-7 Phenyl Sulphonate, as light-yellow oil of 95% purity.

10.C Preparation of Dibenzyl Ether Vitamin K2-8 SO$_2$Ph
4.14 g (0.01 mol) Geranyl geranyl phenyl sulphonate and 7.96 g (0.012 mol) Dibenzyl ether Vitamin K2-4 Chloride were dissolved in 82.8 ml toluene. 60% w/w 41.4 g aqueous solution of potassium hydroxide was added followed by 0.414 g of tetrabutyl ammonium bromide and 0.207 g 18 crown 6 at 30° C. Reaction mass was stirred vigorously overnight at same temperature. Layers were separated. Toluene layer was washed with distilled water followed by 5% acetic acid, distilled water, brine and dried over anhydrous sodium sulphate. Toluene was distilled under vacuum to yield 12 g of crude Dibenzyl ether Vitamin K2-8 Phenyl Sulphonate as dark red colour oil. Crude product was purified by column chromatography in mixture of hexane and ethyl acetate to yield 9.8 g Dibenzyl ether Vitamin K2-8 Phenyl Sulphonate, as light-yellow oil of 97% purity.

Example 11

Preparation of Vitamin K2

11A. Preparation of Vitamin K2-6

9.05 g (0.01 mol) Dibenzyl ether of Vitamin K2-6 Phenyl Sulphonate was dissolved in 29.1 ml of Tetrahydrofuran under inert atmosphere and 0.01 g of (1,3-Bis (diphenyl phosphino) propane) palladium II chloride was added. The reaction mass was cooled to −5° C. 6.36 g (0.06 mol) super hydride solution was charged over 20 minutes. Reaction mass was stirred at room temperature for 10-12 hours. After completion of the reaction, it was quenched by dropwise addition of methanol followed by acetic acid over 1 hour. The reaction mass was further stirred for 2 hours at room temperature. The solvent was distilled off at 40° C. The residue was dissolved in the mixture of 38 ml dichloromethane and 76 ml acetonitrile, and cooled to 0 to −5° C. Then 15.8 g (0.029 mol) Ceric Ammonium Nitrate (CAN) dissolved in 15 ml acetonitrile and 15 ml water was added in 10-15 minutes. The progress of the reaction was monitored by TLC. After completion of the reaction, the reaction mass was quenched in methylene dichloride and water. The layers were separated and aqueous layer was extracted with methylene dichloride. The two organic layers were mixed and washed with water followed by brine and dried over sodium sulphate. The solvent was distilled under vacuum to give 6.0 g crude product, which was purified by column chromatography using mixture of hexane and ethyl acetate to yield 3.7 g (0.0064 mol) Vitamin K2-6 as bright yellow crystalline solid having melting point 49-50° C. and had 98% purity.

$^1$H NMR characterization data for Vitamin K2-6: $^1$H NMR (400 MHz, CDCl$_3$) δ 8.10 (m, 2H), 7.70 (m, 2H), 5.03 (m, 6H), 3.38 (d, 2H), 2.2 (s, 3H), 1.93-2.07 (m, 20H), 1.81 (s, 3H), 1.69 (s, 3H), 1.61 (s, 9H), 1.58 (s, 3H).

11B. Preparation of Vitamin K2-7

9.71 g (0.01 mol) Dibenzyl ether of Vitamin K2-7 phenyl sulphonate was dissolved in 29.1 ml of Tetrahydrofuran under inert atmosphere and 0.01 gm of (1,3-Bis (diphenyl phosphino) propane) palladium II chloride was added. The reaction mass was cooled to −5° C. 6.36 g (0.06 mol) super hydride solution was charged in 20 minutes. Reaction mass was stirred at room temperature for 10-12 hours. It was then quenched by dropwise addition of methanol followed by acetic acid over 1 hour. The reaction mass was further stirred for 2 hours at room temperature.

The solvent was distilled off at 40° C. The residue was dissolved in the mixture of 40 ml dichloromethane and 80 ml acetonitrile and cooled 0 to −5° C. Then 15.8 g (0.029 mol) Ceric Ammonium Nitrate (CAN) dissolved in 15 ml acetonitrile and 15 ml water was added over 10-15 minutes. Progress of the reaction was monitored by TLC. After completion of the reaction, the reaction mass was quenched in methylene dichloride and water. The layers were separated, and aqueous layer was extracted with methylene dichloride. The two organic layers were combined and washed with water followed by brine and dried over sodium sulphate. The solvent was distilled under vacuum to give 6.5 g crude product which was purified by column chromatography using a mixture of hexane and ethyl acetate to yield 4 g (0.0062 mol) Vitamin K2-7 as bright yellow crystalline solid having melting point 54-55° C. having 98% purity.

$^1$H NMR characterization data for Vitamin K2-7: $^1$H NMR (400 MHz, CDCl$_3$) δ 8.10 (m, 2H), 7.71 (m, 2H), 5.08-5.14 (m, 7H), 3.38 (d, 2H), 2.21 (s, 3H), 1.97-2.09 (m, 24H), 1.81 (s, 3H), 1.70 (s, 3H), 1.58-1.61 (m, 18H).

11C. Preparation of Vitamin K2-8

10.4 g (0.01 mol) Dibenzyl ether of Vitamin K2-8 Phenyl Sulphonate was dissolved in 29.1 ml of Tetrahydrofuran under inert atmosphere and 0.01 g (1,3-Bis (diphenyl phosphino) propane) palladium II chloride was added. The reaction mass was cooled to −5° C. 6.36 g (0.06 mol) super hydride solution was charged in 20 minutes. Reaction mass was stirred at room temperature for 10-12 hours. After completion of reaction, it was quenched by dropwise addition of methanol followed by acetic acid in 1 hour. The reaction mass was stirred further for 2 hours at room temperature. The solvent was distilled off at 40° C. The residue was dissolved in the mixture of 43 ml dichloromethane and 86 ml acetonitrile and cooled to 0 to −5° C. 15.8 g (0.029 mol) Ceric Ammonium Nitrate (CAN) dissolved in 15 ml acetonitrile and 15 ml water was added over 10-15 minutes at same temperature. The progress of the reaction was monitored by TLC. After completion of the reaction, the reaction mass was quenched in methylene dichloride and water. The layers were separated and aqueous layer was extracted with methylene dichloride. The two organic layers were combined, washed with water followed by brine and dried over sodium sulphate. The solvent was distilled under vacuum to yield 7 g crude product, which was purified by column chromatography using mixture of hexane and ethyl acetate to yield 4.2 g (0.0058 mol) Vitamin K2-8 as bright yellow crystalline solid having melting point 58-59° C. and 98% purity.

$^1$H NMR characterization data for Vitamin K2-8: $^1$H NMR (400 MHz, CDCl$_3$) δ 8.10 (m, 2H), 7.71 (m, 2H), 5.04-5.15 (m, 8H), 3.40 (d, 2H), 2.21 (s, 3H), 1.97-2.09 (m, 28H), 1.81 (s, 3H), 1.70 (s, 3H), 1.58-1.61 (m, 21H).

What is claimed is:

1. A process for the synthesis of Vitamin K2 of Formula I,

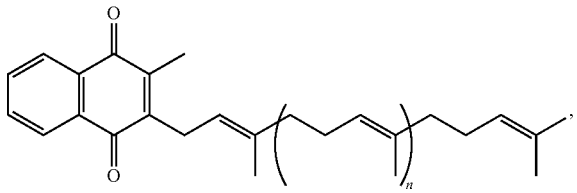

Formula I wherein n is 3 or 4, and the process comprises:

(a) adding menadione/cyclopentadiene adduct to t-butanol:toluene mixture that is in the range of 10:90 to 20:80 v/v, at a temperature ranging from 20° C. to 40° C.;

(b) dissolving potassium t-butoxide in reaction mixture of (a);

(c) adding prenyl chloride to the reaction mixture of (b) and stirring the mixture for an hour;

(d) quenching the reaction mixture of (c) in distilled water;

(e) adjusting the pH of the reaction mixture of (d) to 5-6 and isolating the non-aqueous layer;

(f) washing the non-aqueous layer of (e) with water and brine, and drying the washed non-aqueous layer over sodium sulfate;

(g) recovering the product Vitamin K2-3 from the non-aqueous layer of (f) by reflux and distilling off the solvent under vacuum, wherein Vitamin K2-3 has the chemical structure:

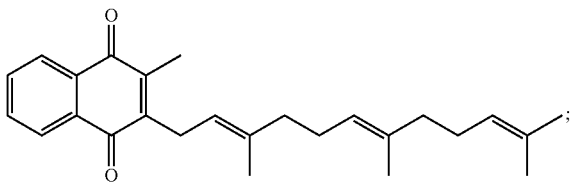 [SMILES: CC(C)=CCC/C(C)=C/CC/C(C)=C/CC1=C(C)C(=O)c2ccccc2C1=O]

(h) converting the Vitamin K2-3 obtained in (g) into its dibenzyl ether having the chemical structure:

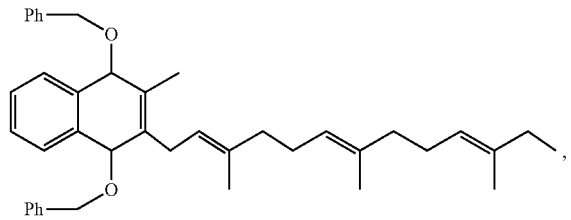

wherein Ph is a phenyl group;

(i) converting the dibenzyl ether of Vitamin K2-3 obtained in (h) into its bromohydrin derivative in the presence of N-bromo succinamide and tetrahydrofuran, wherein the bromohydrin derivative of dibenzyl ether of vitamin K2-3 has the chemical structure:

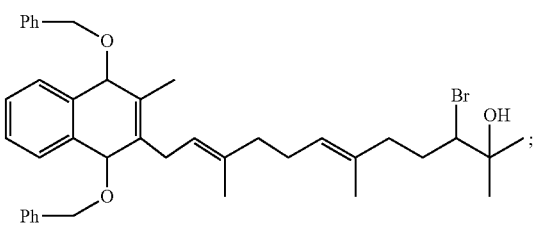 [SMILES: CC1=C(C/C=C(\C)CC/C=C(\C)CCC(Br)C(C)(C)O)C(OCc2ccccc2)c2ccccc2C1OCc1ccccc1]

(j) converting the bromohydrin derivative of dibenzyl ether of vitamin K2-3 obtain in (i) to its epoxide in the presence of potassium carbonate and methanol, wherein the epoxide derivative of dibenzyl ether of vitamin K2-3 has the chemical structure:

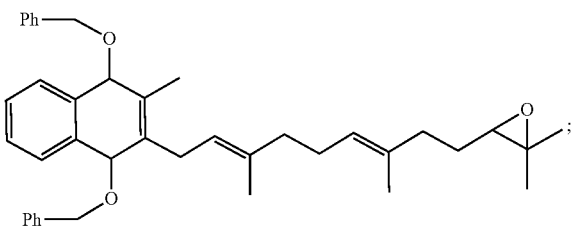 [SMILES: CC1=C(C/C=C(\C)CC/C=C(\C)CCC2OC2(C)C)C(OCc2ccccc2)c2ccccc2C1OCc1ccccc1]

(k) converting the epoxide derivative of dibenzyl ether of vitamin K2-3 obtained in (j) into Vitamin K2-3 alcohol in the presence of aluminium isopropoxide in toluene, wherein the Vitamin K2-3 alcohol has the chemical structure:

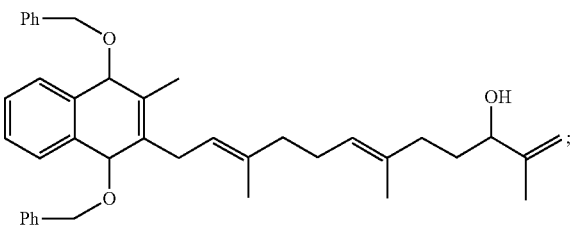 [SMILES: C=C(C)C(O)CC/C(C)=C/CC/C(C)=C/CC1=C(C)C(OCc2ccccc2)c2ccccc2C1OCc1ccccc1]

(l) reacting the Vitamin K2-3 alcohol obtained in (k) with thionyl chloride in hexane to form Vitamin K2-3 chloride having the chemical structure:

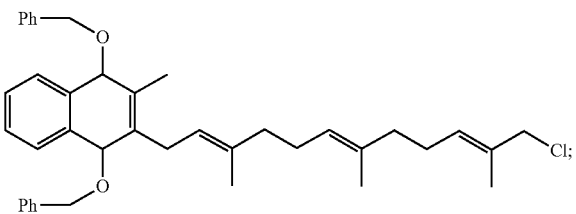 [SMILES: CC1=C(C/C=C(\C)CC/C=C(\C)CC/C=C(\C)CCl)C(OCc2ccccc2)c2ccccc2C1OCc1ccccc1]

(m) reacting the Vitamin K2-3 chloride obtained in (l) with a prenyl phenyl sulphonate to obtain a compound, wherein the prenyl phenyl sulphonate is selected from:

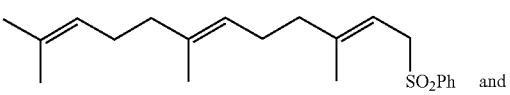 and

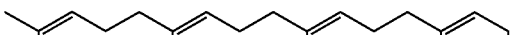

(n) desulphonating, deprotecting, and oxidizing the compound obtained in (m) to obtain Vitamin K2 of Formula I.

2. The process of claim 1, wherein n is 4.

3. The process of claim 1, wherein n is 3.

* * * * *